United States Patent
Chang et al.

(10) Patent No.: US 10,736,609 B2
(45) Date of Patent: Aug. 11, 2020

(54) ULTRASOUND IMAGING APPARATUS AND METHOD OF CONTROLLING THE SAME

(71) Applicant: SAMSUNG ELECTRONICS CO., LTD., Suwon-si (KR)

(72) Inventors: Jungwoo Chang, Seoul (KR); Sunkwon Kim, Suwon-si (KR); Won-Chul Bang, Seongnam-si (KR); Jiwon Ryu, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1079 days.

(21) Appl. No.: 14/818,536

(22) Filed: Aug. 5, 2015

(65) Prior Publication Data
US 2016/0113630 A1 Apr. 28, 2016

(30) Foreign Application Priority Data
Oct. 23, 2014 (KR) .................. 10-2014-0144463

(51) Int. Cl.
| | |
|---|---|
| A61B 8/00 | (2006.01) |
| A61B 8/08 | (2006.01) |
| A61B 8/14 | (2006.01) |
| G06T 3/00 | (2006.01) |
| G06T 7/30 | (2017.01) |

(52) U.S. Cl.
CPC .............. *A61B 8/5238* (2013.01); *A61B 8/14* (2013.01); *A61B 8/4245* (2013.01); *A61B 8/463* (2013.01); *A61B 8/5261* (2013.01); *G06T 3/0012* (2013.01); *G06T 7/30* (2017.01); *G06T 2207/10072* (2013.01); *G06T 2207/10132* (2013.01); *G06T 2207/20081* (2013.01); *G06T 2207/20084* (2013.01); *G06T 2207/30244* (2013.01)

(58) Field of Classification Search
None
See application file for complete search history.

(56) References Cited

U.S. PATENT DOCUMENTS

| | | | | |
|---|---|---|---|---|
| 2010/0055657 | A1* | 3/2010 | Goble | G09B 23/286 434/262 |
| 2011/0021915 | A1* | 1/2011 | Feng | A61B 5/7267 600/443 |
| 2012/0189178 | A1* | 7/2012 | Seong | G06T 11/008 382/128 |
| 2014/0051986 | A1* | 2/2014 | Zhao | A61B 5/066 600/424 |
| 2014/0254900 | A1* | 9/2014 | Sturm | A61B 5/0037 382/128 |

\* cited by examiner

*Primary Examiner* — Joel F Brutus
(74) *Attorney, Agent, or Firm* — Sughrue Mion, PLLC

(57) ABSTRACT

An ultrasound imaging apparatus includes an image generator configured to scan an object to obtain an ultrasound image; a neural network configured to generate a virtual ultrasound image based on matching medical images of different modalities; an image converting part configured to convert a medical image of a different modality, previously obtained by scanning the object, into the virtual ultrasound image by using the neural network; and a matching part configured to determine a position of a virtual probe based on the ultrasound image and the virtual ultrasound image, and configured to match the ultrasound image with the medical image that corresponds to the determined position of the virtual probe.

18 Claims, 18 Drawing Sheets

ULTRASOUND IMAGING APPARATUS AND METHOD OF CONTROLLING THE SAME

CROSS-REFERENCE TO RELATED APPLICATION

This application claims priority from Korean Patent Application No. 10-2014-0144463, filed on Oct. 23, 2014, in the Korean Intellectual Property Office, the disclosure of which is incorporated herein by reference in its entirety.

BACKGROUND

1. Field

Apparatuses and methods consistent with exemplary embodiments relate to obtaining an ultrasound image from an object.

2. Description of the Related Art

An ultrasound imaging apparatus applies ultrasound to an object, detects the ultrasound, i.e. echoes, reflected from the object, and generates an image of a region of the object being examined, such as a cross section of soft tissue or a blood flow, based on the detected ultrasound to provide information about the region being examined.

The ultrasound imaging apparatus has an advantage in that the ultrasound imaging apparatus can obtain an image in real time. However, it may be difficult to distinguish an outline, an internal structure, or lesion of an organ in an ultrasound image because of noises included therein.

In recent years, a medical image obtained from another medical apparatus that is matched with an ultrasound image is provided for the purpose of performing accurate diagnosis or delicate procedure on an object. For example, a magnetic resonance image that has relatively free scanning conditions and an excellent contrast and provides various images of soft tissue or a computed tomogram having a higher resolution may be matched with an ultrasound image and provided.

SUMMARY

One or more exemplary embodiments provide an ultrasound imaging apparatus for matching a previously obtained medical image and an ultrasound image obtained by scanning an object to provide the matched image and a method of controlling the same.

According to an aspect of an exemplary embodiment, there is provided an ultrasound imaging apparatus, which includes: an image generator configured to scan an object to obtain an ultrasound image; a neural network trained for generation of a virtual ultrasound image based on matched images; an image converting part configured to convert a medical image previously obtained by scanning the object into the virtual ultrasound image using the neural network; and a matching part configured to determine a position of a virtual probe to be applied to the medical image based on the ultrasound image and the virtual ultrasound image and to match the ultrasound image and the medical image based on the position of the virtual probe.

Here, the matching part may determine the position of the virtual probe based on an error between the ultrasound image and the virtual ultrasound image.

Further, the image converting part may generate the virtual ultrasound image based on the position of the virtual probe.

Further, the image converting part may select a first region from the medical image based on the position of the virtual probe, input the selected first region into the neural network, and obtain an image of a second region of the virtual ultrasound image.

Here, the first region may have a length determined based on a range of ultrasound in the object, and a width determined based on a resolution of the ultrasound image.

Further, the ultrasound imaging apparatus may further include a learning part configured to train the neural network using the ultrasound image and the medical image that are matched at the matching part.

The medical image may include one of a magnetic resonance (MR) image, a computed tomography (CT) image, a positron emission tomography (PET) image, and a single photon emission computed tomography (SPECT) image.

Further, when the matched medical image is input, the learning part may train the neural network such that the ultrasound image matched with the medical image is output.

In addition, the neural network may have a multilayer perceptron structure.

According to an aspect of an exemplary embodiment, there is provided a method of controlling an ultrasound imaging apparatus, which includes: scanning an object to obtain an ultrasound image; converting a medical image previously obtained by scanning the object into a virtual ultrasound image using a neural network trained for generation of the virtual ultrasound image based on matched images; and determining a position of a virtual probe to be applied to the medical image based on the ultrasound image and the virtual ultrasound image and matching the ultrasound image and the medical image based on the position of the virtual probe.

Here, the converting of the medical image may include converting the medical image into the virtual ultrasound image based on the position of the virtual probe set for the medial image.

Further, the matching of the ultrasound image and the medical image may include resetting the position of the virtual probe based on an error between the ultrasound image and the virtual ultrasound image.

Further, the matching of the ultrasound image and the medical image may further include applying the neural network to the medical image and generating the virtual ultrasound image based on the reset position of the virtual probe.

In addition, the matching of the ultrasound image and the medical image further may include matching the medial image and the ultrasound image based on the position of the virtual probe.

Further, the converting of the medical image may include: selecting a first region from the medical image based on the position of the virtual probe; and inputting the selected first region into the neural network to obtain an image of a second region of the virtual ultrasound image.

Here, the first region may have a length determined based on a range of ultrasound in the object, and a width obtained based on a resolution of the ultrasound image.

In addition, the method may further include training the neural network using the medical image and the ultrasound image that are matched with each other in the matching of the ultrasound image and the medical image.

As described above, the medical image and the ultrasound image are matched using the previously trained neural network, and thus the medical image and the ultrasound image can be more precisely matched.

BRIEF DESCRIPTION OF THE DRAWINGS

The above and/or other aspects will become more apparent by describing certain exemplary embodiments with reference to the accompanying drawings.

DETAILED DESCRIPTION

Figure 1:
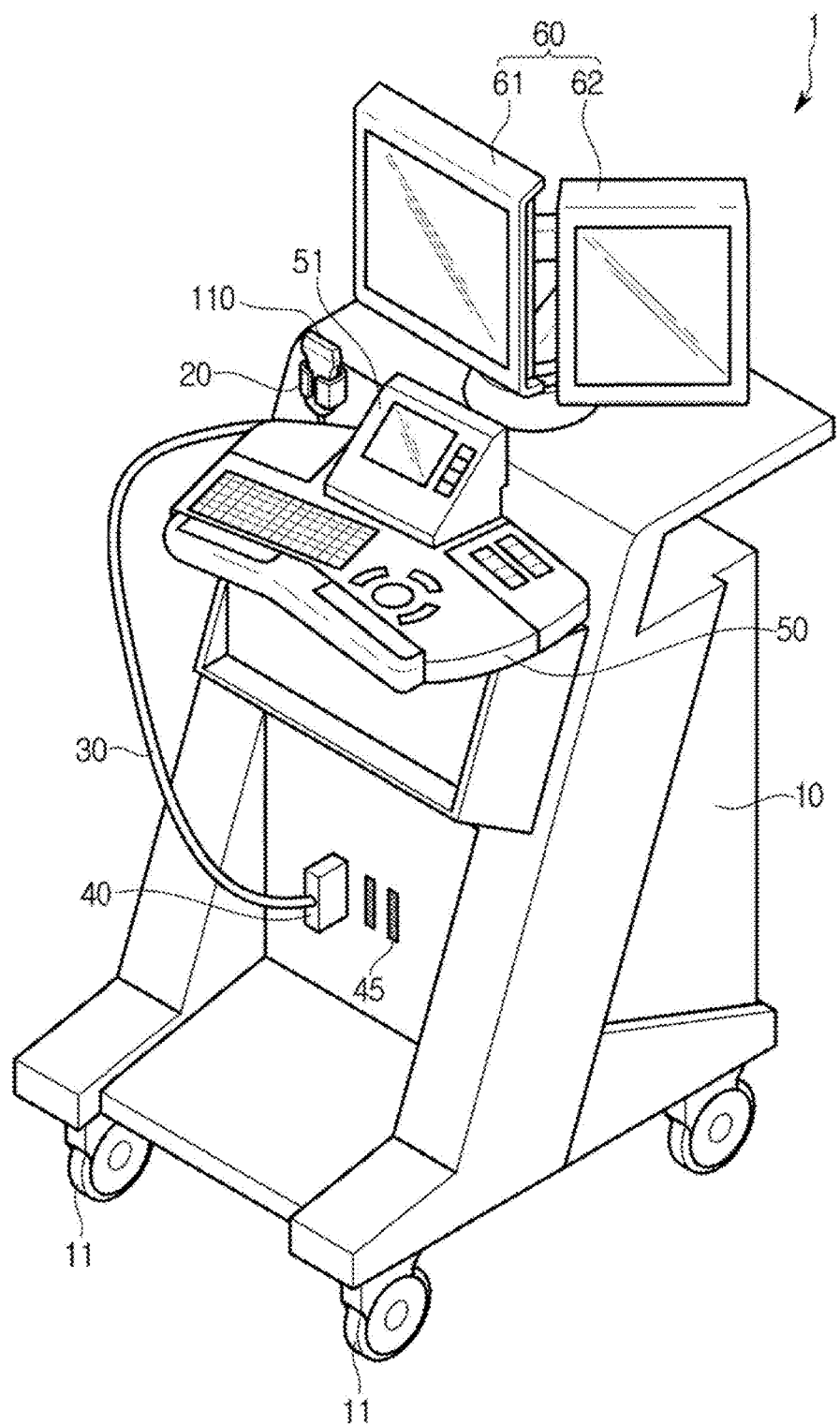
FIG. 1 is a perspective view illustrating an ultrasound imaging apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail The terms used in the disclosure are selected as general terms used currently as widely as possible upon consideration of the functions made in the disclosure, but they may be varied according to the intention or practices of those of ordinary skill in the art, and the advent of new technology. Further, in specific case, terms arbitrarily selected by the applicant are also used, and in this case, its meanings are mentioned in corresponding detailed description section, so the disclosure should be understood not by lexical meanings of the terms but by given meanings of the terms.

It will be understood that, when it is described that some parts "include" some components, this description does not exclude the presence of other components throughout the specification, unless otherwise described in particular. In addition, the terms "section," "module," "unit," etc. used herein refer to the unit processing at least one of a function and an operation, which can be realized by software, hardware such as a field programmable gate array (FPGA) or an application-specific integrated circuit (ASIC), or a combination thereof. However, such components are not limited to the software or the hardware. Each of the components may be stored in an addressable storage medium or may be configured so as to implement one or more processors. Accordingly, the constituent components may include, for example, software, object-oriented software, classes, tasks, processes, functions, attributes, procedures, sub-routines, and segments of program codes, drivers, firmware, micro codes, circuits, data, database, data structures, tables, arrays, variables or the like.

While such terms as "first," "second," etc., may be used to describe various components, such components must not be limited to the above terms. The above terms are used only to distinguish one component from another. For example, a first component may be referred to as a second component without departing from the scope of the disclosure, and likewise a second component may be referred to as a first component. The term "and/or" encompasses both combinations of multiple relevant items and any one of the multiple relevant items.

An ultrasound imaging apparatus according to an exemplary embodiment can scan an object to match the obtained ultrasound image with a medical image obtained from another modality of apparatus. For example, the medial image may be one of a magnetic resonance (MR) image, a computed tomography (CT) image, a positron emission tomography (PET) image, and a single photon emission computed tomography (SPECT) image.

FIG. 1 is a perspective view illustrating an ultrasound imaging apparatus according to an exemplary embodiment.

As illustrated in FIG. 1, the ultrasound imaging apparatus 1 includes an ultrasound probe 110, a main body 10, an operating panel 50, and a display 60.

The main body 10 may be provided with at least one female connector 45 in the front lower side thereof. A male connector 40 provided at one end of a cable 30 may be physically coupled to the female connector 45. The ultrasound probe 110 and the main body 10 may be connected via the cable 30.

The main body 10 may be provided with multiple casters 11 at a lower portion thereof to secure mobility of the ultrasound imaging apparatus 1. A user can fix the ultrasound imaging apparatus 1 at a specific place or move the ultrasound imaging apparatus 1 in a specific direction using the multiple casters 11. In other words, the ultrasound imaging apparatus 1 may be a cart-type ultrasound imaging apparatus.

Alternatively, the ultrasound imaging apparatus 1 of FIG. 1 may be a portable ultrasound imaging apparatus that can be easily carried by a user. Here, the portable ultrasound imaging apparatus 1 may omit the casters 11. The portable ultrasound imaging apparatus 1 may include, but not limited to, a picture archiving and communications system (PACS)

viewer, a smart phone, a lap-top computer, a personal digital assistant (PDA), a tablet personal computer (PC), or the like.

The ultrasound probe 110 is a portion that comes into contact with a skin of the object, and transmits and/or receives ultrasound to and/or from the object ob. In detail, the ultrasound probe 110 generates the ultrasound according to an input pulse, transmits the ultrasound to an interior of the object ob, and receives reflected ultrasound, i.e. echoes, from a region of the interior of the object ob.

The operating panel 50 is a portion that receives instructions associated with operations of the ultrasound imaging apparatus 1. The user may input instructions for performing diagnosis start, diagnosis region selection, diagnosis type selection, mode selection of a finally output ultrasound image, etc. via the operating panel 50. Modes of the ultrasound image may include an amplitude mode (A-mode), a brightness mode (B-mode), a Doppler mode (D-mode), an elastography mode (E-mode), and a motion mode (M-mode) by way of example.

Further, the user may input instructions relevant to the image matching via the operating panel 50. For example, the user may input a virtual probe position into the medical image and/or adjust the image matching via the operating panel 50.

In an exemplary embodiment, as illustrated in FIG. 1, the operating panel 50 may be located at an upper portion of the main body 10. Here, the operating panel 50 may include at least one of, for example, a switch, a key, a wheel, a joystick, a track ball, and a knob.

The operating panel 50 may further include a sub-display 51. The sub-display 51 is provided on one side of the operating panel 50, and may display information associated with the operations of the ultrasound imaging apparatus 1.

For example, the sub-display 51 may display a menu, a guideline, etc. for setting the ultrasound imaging apparatus 1 or adjust current setting of the ultrasound imaging apparatus 1.

Here, the sub-display 51 may be implemented as a touch panel. When the sub-display 51 is implemented as the touch panel, the user may touch the sub-display 51 to input control instructions.

The sub-display 51 is implemented as, for instance, a liquid crystal display (LCD) panel, a light-emitting diode (LED) panel, or an organic light-emitting diode (OLED) panel.

At least one holder 20 for the ultrasound probe 110 may be provided near the operating panel 50 to hold the ultrasound probe 110 in place. Thus, the user can hold the ultrasound probe 110 in the holder 20 of the ultrasound probe 110 when the ultrasound imaging apparatus 1 is not used.

The display 60 may display the ultrasound images obtained during the ultrasound diagnosis. As illustrated in FIG. 1, the display 60 may be mounted on the main body 10 integrally or separately.

Furthermore, the display 60 may include multiple first and second displays 61 and 62 to display different images at the same time. For example, the first display 61 scans the object ob to display the obtained ultrasound medial image, and the second display 62 may display a medical image that matches the obtained ultrasound medical image. The first display 61 may scan the object ob to display the obtained two-dimensional (2D) image, and the second display 62 may display a three-dimensional (3D) image.

Each of the displays 61 and 62 may employ a display such as a plasma display panel (PDP), an LCD panel, an LED panel, an OLED panel, or an active-matrix organic light-emitting diode (AMOLED) panel.

Figure 2:
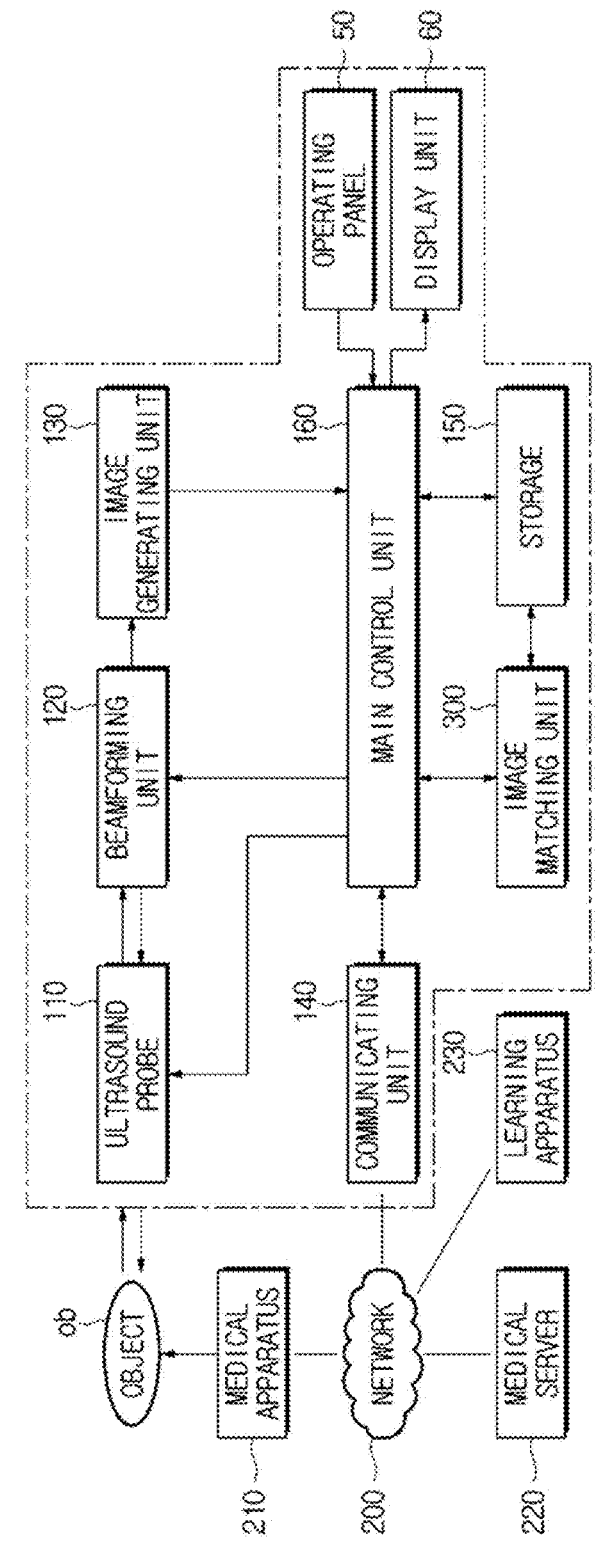
FIG. 2 is a control block diagram of the ultrasound imaging apparatus according to an exemplary embodiment.

FIG. 2 is a control block diagram of the ultrasound imaging apparatus 1 according to an exemplary embodiment. Referring to FIG. 2, the ultrasound imaging apparatus 1 according to an exemplary embodiment includes the ultrasound probe 110, a beamformer 120, an image generator 130, a communicator 140, a storage 150, an image matcher 300, a main controller 160, the operating panel 50, and the display 60.

The communicator 140 is connected to another apparatus, and may transmit and/or receive data to and/or from the connected other apparatus. The communicator 140 may be connected to another apparatus connected to a network 200, and may receive various data for performing the image matching. For example, the communicator 140 may receive a neural network 320 (see FIG. 3) for performing the image matching from another apparatus to be transmitted to the image matcher 300, or receive a medical image to be used for the image matching from another apparatus.

In detail, the communicator 140 may receive a trained the neural network 320 from a learning apparatus 230. Here, the learning apparatus 230 is an apparatus for training the neural network 320, and may supervise and train the neural network 320 by using training data.

Further, the communicator 140 may receive the medical image obtained by scanning the object ob from a medical apparatus 210. In this way, the medical image received through the communicator 140 may be stored in the storage 150 and used to generate a matched image.

Here, the medical apparatus 210 is designed to scan the object ob to obtain the medical image according to a preset method. The medical apparatus 210 may be an apparatus having a modality different from that of the ultrasound imaging apparatus 1. For example, the medical apparatus 210 may be one of a magnetic resonance imaging (MRI) apparatus, a computed tomography (CT) apparatus, a positron emission tomography (PET) apparatus, and a single photon emission computed tomography (SPECT) apparatus.

Further, the communicator 140 may receive information, such as diagnosis records, a treatment schedule, etc. of the object ob, which is stored in a medical server 220, and medical images obtained using the medical apparatus 210, and/or transmit the ultrasound image obtained based on echo signals to the medical server 220.

Here, the medical server 220 administrates medical information that can be used in diagnosis and treatment of the object ob. For example, the medical server 220 may administrate the information, such as diagnosis records, a treatment schedule, etc. of the object ob. Further, the medical server 220 may receive and/or administrate the medical image from the medical apparatus 210, and transmit the stored medical image to the ultrasound imaging apparatus 1 according to a request from the ultrasound imaging apparatus 1.

Further, the communicator 140 may perform data communication with another apparatus according to various wired and/or wireless communication protocols, for example, according to the digital imaging and communications in medicine (DICOM) standard.

The ultrasound probe 110 comes into contact with the skin of the object ob, transmits the ultrasound to the object ob, and receives the reflected ultrasound, i.e. the echoes. To this end, the ultrasound probe 110 may include a transducer. Here, the transducer T refers to a device that converts a given form of energy into another form of energy. For example, the transducer T may convert electrical energy into wave energy, or vice versa.

In detail, the transducer T may include a piezoelectric material or a piezoelectric thin film. If an alternating current is applied to the piezoelectric material or the piezoelectric thin film from an internal electricity storage device such as a battery or an external power supply, the piezoelectric material or the piezoelectric thin film vibrates at a predetermined frequency, and ultrasound of a predetermined frequency is generated according to a vibration frequency.

On the other hand, when ultrasound of a predetermined frequency is received by the piezoelectric material or the piezoelectric thin film, the piezoelectric material or the piezoelectric thin film vibrates according to the frequency of the received ultrasound. Here, the piezoelectric material or the piezoelectric thin film outputs an alternating current of a frequency corresponding to the vibration frequency.

Further, various types of transducers such as a magnetostrictive ultrasonic transducer using a magnetostrictive effect of a magnet, a piezoelectric ultrasonic transducer using a piezoelectric effect of a piezoelectric material, and a capacitive micromachined ultrasonic transducer (cMUT) transceiving ultrasound using vibration of several hundreds or thousands of micromachined thin films may be used as the transducer T. In addition, different types of devices that can generate ultrasound according to an electrical signal or generate an electrical signal according to ultrasound may be used as the transducer T.

The beamformer 120 may apply a drive signal to the ultrasound probe 110, and/or beamform the echo signal received from the ultrasound probe 110.

To be specific, the beamformer 120 applies the drive signal to the ultrasound probe 110. The beamformer 120 generates a drive pulse for forming transmission ultrasound according to a predetermined pulse repetition frequency (PRF), delays and outputs the drive pulse, and focuses the ultrasound transmitted to the object ob.

Further, the beamformer 120 beamforms and outputs the echo signal received from the ultrasound probe 110. In detail, the beamformer 120 may appropriately delay and focus the received echo signal based on reception directionality.

Further, the beamformer 120 may synthesize the delayed output echo signals. Here, the beamformer 120 synthesizes the multiple echo signals to output the synthesized echo signal. The beamformer 120 may synthesize the echo signals by applying a predetermined weighted value to the echo signals. The weighted value applied to the echo signals may be determined regardless of the echo signals, or determined based on the echo signals.

The image generator 130 generates an ultrasound image based on the echo signal output from the beamformer 120. For example, the image generator 130 may generate at least one of an amplitude mode (A-mode) image, a brightness mode (B-mode) image, a Doppler mode (D-mode) image, an elastography mode (E-mode) image, and a motion mode (M-mode) image based on the echo signal. Furthermore, the image generator 130 may generate a 3D ultrasound image based on multiple ultrasound images obtained from the echo signals.

Here, the image generator 130 may correspond to one or more processors. The processor may be implemented as an array of numerous logic gates, or a combination of a general-purpose microprocessor and a memory in which a program capable of being executed by the microprocessor is stored. For example, the image generator 130 may be implemented as a general-purpose graphic processing unit (GPU).

The storage 150 stores various pieces of information for driving the ultrasound imaging apparatus 1. For example, the storage 150 may store image information about the diagnosis of the object ob, such as the echo signal and the ultrasound image, and store a program for driving the ultrasound imaging apparatus 1.

Further, the storage 150 may store the medical image received via the communicator 140. Here, the medical image is obtained from the medical apparatus 210 having a modality different from that of the ultrasound imaging apparatus 1, and may be transmitted from the medical server 220 or the medical apparatus 210 connected through the network 200.

Further, the storage 150 may include, but not limited to, a high-speed random access memory (RAM), a magnetic disc, a static random access memory (SRAM), a dynamic random access memory (DRAM), or a read-only memory (ROM).

Further, the storage 150 can be removably coupled with the ultrasound imaging apparatus 1. For example, the storage 150 may include, but not limited to, a compact flash (CF) card, a secure digital (SD) card, a smart media (SM) card, a multimedia (MM) card, or a memory stick. Further, the storage 150 may be provided outside the ultrasound imaging apparatus 1, and may transmit or receive data to or from the ultrasound imaging apparatus 1 by wire or wireless.

The main controller 160 may control an overall operation of the ultrasound imaging apparatus 1. In detail, the main controller 160 controls each component to generate the ultrasound image of the object ob, and may match and display the generated ultrasound image and a prestored medical image.

Further, the main controller 160 controls the communicator 140 such that the medical image to be matched with the ultrasound image is received, and may store the medical image received via the communicator 140 in the storage 150.

Further, the main controller 160 may correspond to one or more processors. Here, the processor may be implemented as an array of numerous logic gates, or a combination of a general-purpose microprocessor and a memory in which a program capable of being executed by the microprocessor is stored.

The image matcher 300 may match, under the control of the main controller 160, the ultrasound image obtained by scanning the object ob and the medical image previously obtained by scanning the object ob. Hereinafter, the image matcher for matching the ultrasound image and the medical image will be described in detail.

Figure 3:
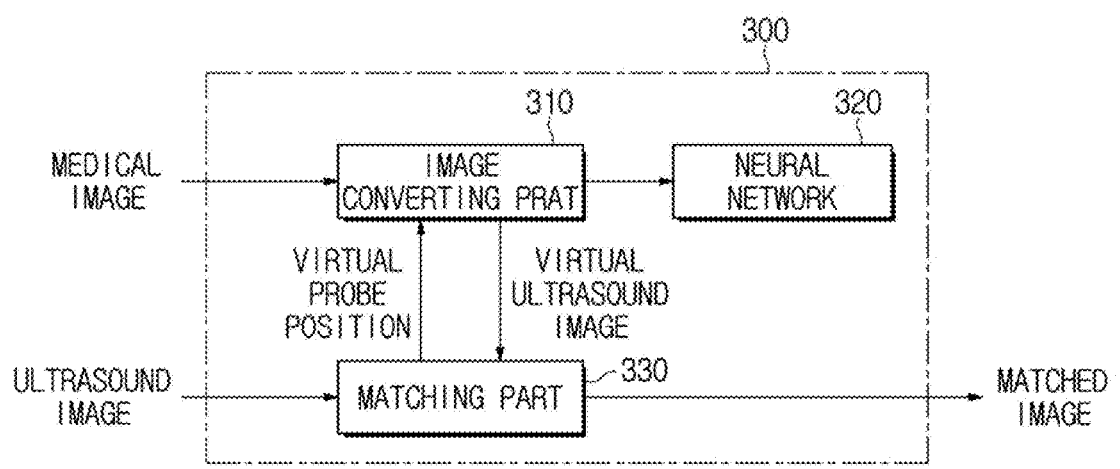
FIG. 3 is a control block diagram for describing an image matcher of the ultrasound imaging apparatus according to an exemplary embodiment.

FIG. 3 is a control block diagram for describing an example of an image matcher of the ultrasound imaging apparatus.

As illustrated in FIG. 3, the image matcher 300 may include an image converting part 310 that converts a medical image into a virtual ultrasound image, and a matching part 330 that matches an ultrasound image obtained by scanning the object ob and the virtual ultrasound image generated by the image converting part 310.

The image converting part 310 may convert the medical image into the virtual ultrasound image using the previously trained neural network 320. Hereinafter, prior to describing an operation of the image converting part 310, the neural network 320 will be described.

The neural network 320 is designed to engineeringly model a human brain structure at which an efficient function of recognition occurs. The neural network 320 may be implemented as hardware, software, or a combination thereof.

The human brain includes a basic unit of a nerve called a neuron. Each neuron is connected to each other through a synapse and can process information in a nonlinear and/or parallel way.

The neural network 320 includes multiple units corresponding to the neurons, and the multiple units may be interconnected to each other with a predetermined connection strength. The neural network 320 that can be used to generate the virtual ultrasound image in this way has no limitation. For example, the neural network 320 may be a convolutional neural network.

Figure 4:
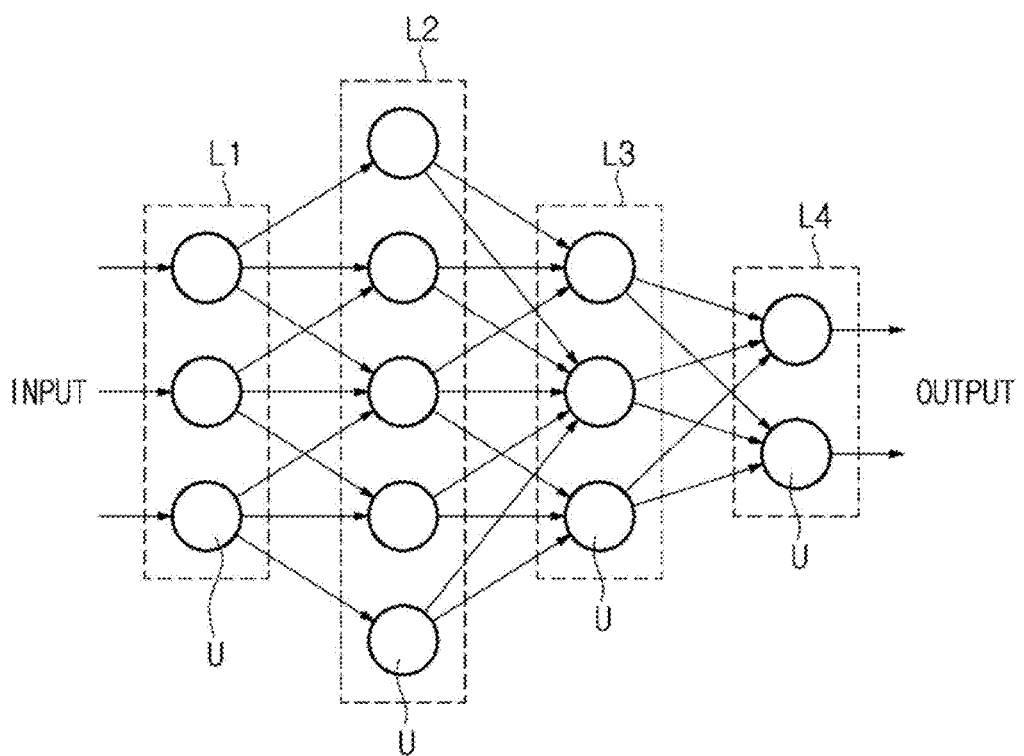
FIG. 4 is a schematic view illustrating an example of a neural network.

FIG. 4 is a schematic view illustrating an example of the neural network 320.

Referring to FIG. 4, the neural network 320 may include multiple layers L1, L2, L3, and L4 according to a multilayer perceptron structure. Namely, the multiple units U included in the neural network 320 may be classified into the multiple layers L1 to L4.

The neural network 320 of the multilayer perceptron structure is implemented with the multiple layers L1 to L4, and may be trained for a more complicated model.

Further, the units U classified into the multiple layers L1 to L4 may be interconnected to each other with a predetermined connection strength. Here, each unit may be connected to only other units U having a high relation.

Further, an output signal output from the output layer L4 of the neural network 320 may have a lower dimension than an input signal input via the input layer L1. In other words, when M input signals are input to the input layer L1, N output signals may be output from the output layer L4, wherein N is less than M.

FIG. 4 illustrates only an example of the neural network 320. The neural network 320 may include more layers, and a connection form of each unit may vary. For example, each unit may be connected to only other units included in the neighboring layer according to a restricted Boltzmann machine structure.

The human brain is trained by adjusting the connection form or strength of the synapse. That is, the brain is trained by adjusting the connection strength of the synapse in such a way that the brain weakens connection between the neurons leading to an error of an incorrect answer and reinforces the connection between the neurons leading to a correct answer.

The neural network 320 is trained by imitating the aforementioned training way of the human brain. Here, the training refers to searching and generalizing a pattern from predetermined training data. The neural network 320 is trained in such a manner that the connection between the neurons leading to the correct answer is reinforced. Hereinafter, an example of the training way of the neural network 320 will be described.

Figure 5:
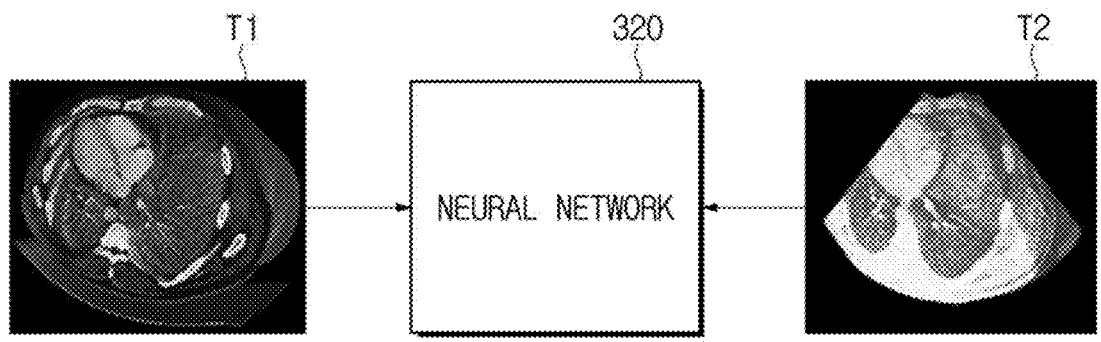
FIG. 5 is a view for describing supervised learning of a neural network.

FIG. 5 is a view for describing supervised learning of a neural network.

As illustrated in FIG. 5, the neural network 320 may be an object of supervised learning. The supervised learning is a method of training the neural network 320 using training data including input and output data. A correlation between the input and output data may be trained through the supervised learning.

In the training data of the neural network 320, an ultrasound image T2 and a medial image T1 that are matched with each other may be used as the training data for training the neural network 320. The medical image T1 may serve as input data, and the ultrasound image T2 may serve as output data.

The neural network 320 is trained in such a manner that the virtual ultrasound image output in response to the input medical image T1 corresponds to the ultrasound image T2 that is the output data. Namely, the neural network 320 is trained to convert the medial image T1 into the virtual ultrasound image by the training data.

A plurality of pieces of training data may be used for the training of the neural network 320. In this way, the neural network 320 may be trained to increase training precision the plurality of training data. For example, the training data may be large size data.

The supervised learning of the neural network 320 may be carried out by the ultrasound imaging apparatus 1 according to an exemplary embodiment, however, the supervised learning of the neural network 320 may be carried out by the learning apparatus 230 connected to the network 200 as described above.

Hereinafter, for convenience of the description, the neural network 320 will be described to be trained by the learning apparatus 230 provided separate from the ultrasound imaging apparatus 1. However, the neural network 320 may be trained by the ultrasound imaging apparatus 1.

Figure 6:
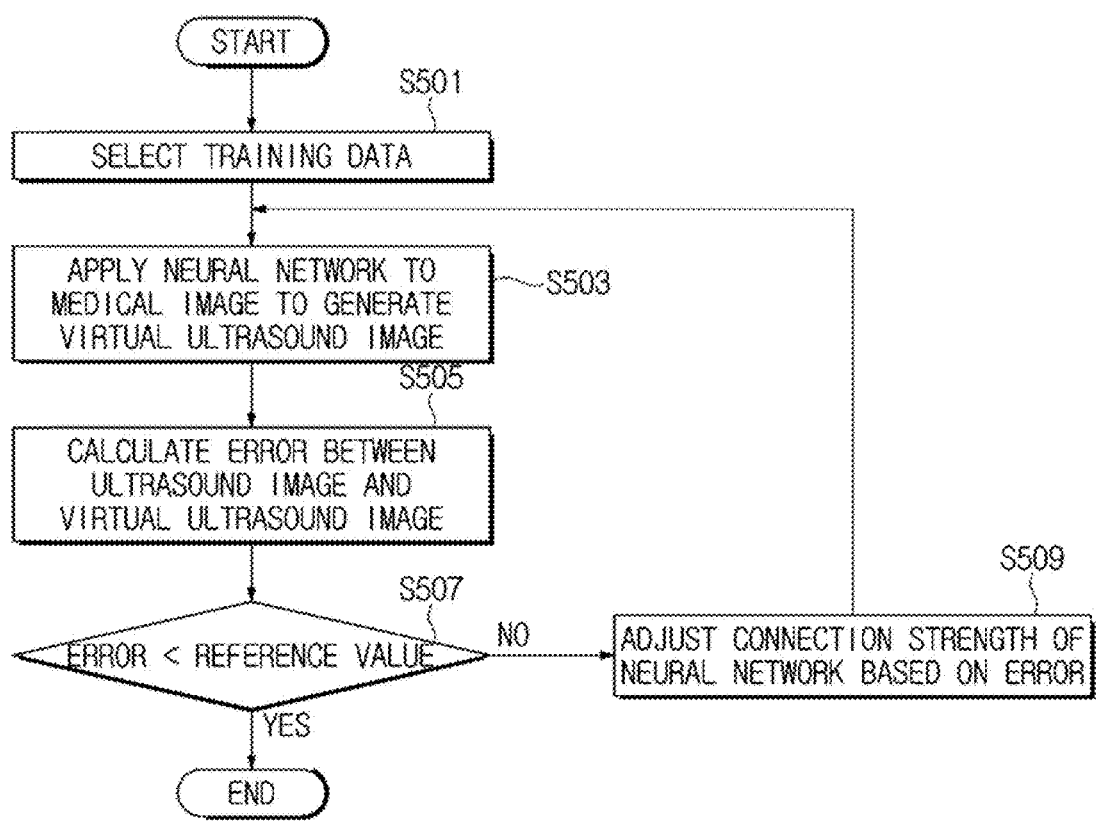
FIG. 6 is a flow chart for describing an example of a training method of a neural network.

FIG. 6 is a flow chart for describing an example of the training method of the neural network 320.

Referring to FIG. 6, the learning apparatus 230 selects training data from a set of training data (S501). Since the plurality of pieces of training data may be used to train the neural network 320 as described above, the learning apparatus 230 may select the training data to be used for the training from among the set of the plurality of training data. For example, the training data may include a medical image as input data and an ultrasound image as output data.

The learning apparatus 230 applies the neural network 320 to the medical image of the training data and generates a virtual ultrasound image (S503). The learning apparatus 230 calculates an error between the ultrasound image of the training data and the virtual ultrasound image (S505). If the calculated error is smaller than a reference value ('Yes' to S507), the learning apparatus 230 terminates the training.

If the calculated error is greater than the reference value ('No' to S507), the learning apparatus 230 adjusts the connection strength of the neural network 320 based on the error (S509). In detail, the learning apparatus 230 may adjust the connection strength of the neural network 320 according to an error backpropagation algorithm such that the error between the virtual ultrasound image generated based on the input medial image and the ultrasound image matched with the medical image is reduced.

In this way, the process of applying the neural network 320 to the medical image to generate the virtual ultrasound image, the process of calculating the error between the virtual ultrasound image and the ultrasound image matched with the medical image, and the process of updating the connection strength based on the error are repetitively performed, and thus the neural network 320 is trained.

Figure 7:
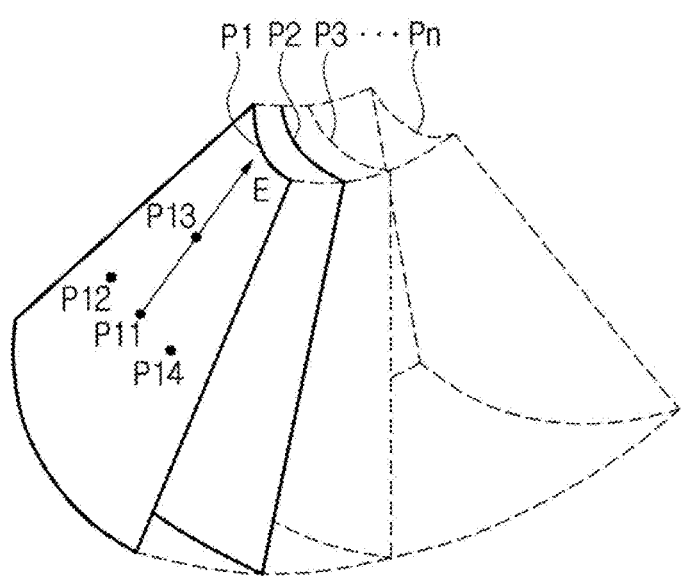
FIG. 7 is a view for describing a feature of an ultrasound image.

Features of the ultrasound image may be considered for the training of the neural network 320. Hereinafter, the features of the ultrasound image will be described. FIG. 7 is a view for describing features of the ultrasound image.

The ultrasound image is generated based on echo signals reflected from the object ob. In detail, brightness of each region of the ultrasound image is determined according to intensity of echoed ultrasound (or echo signals) reflected back from each region.

Referring to FIG. 7, for example, a 3D ultrasound image may be generated based on multiple 2-D ultrasound images corresponding first to n-th cross sections P1 to Pn. Here, brightness of a first point P11 on the first cross section P1 is determined according to intensity of echoed ultrasound E reflected back from the first point P11.

Therefore, tissue located corresponding to the third cross section P3 that is located at a relatively distant distance from the first point P11 may be hardly affected by the echoed ultrasound E reflected back from the first point P11.

Tissue located near a travelling path of the echoed ultrasound E reflected back from the first point P11 may influence the echoed ultrasound E reflected back from the first point P11.

For example, when tissue located at a third point P13 reflects most of ultrasound received thereto, a magnitude of the echoed ultrasound may be reduced, and the echoed ultrasound E reflected back from the first point P11 may be attenuated by the tissue located at the third point P13.

Further, the echoed ultrasound E reflected back from the first point P11 may be attenuated or constructed by the echoed ultrasound reflected from the tissue located at the second or fourth point P12 or P14.

The ultrasound features as described above may be considered for the training of the neural network 320. In detail, the neural network 320 may be trained by inputting only the region relevant to each region of the ultrasound image among the medial images. Hereinafter, region selection of the training data will be described in detail.

Figure 8A:
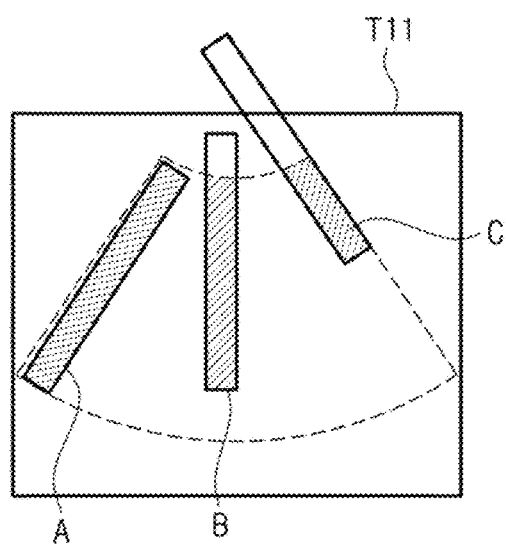
FIGS. 8A and 8B are views for describing an example of region selection of a medical image and an ultrasound image.
Figure 8B:
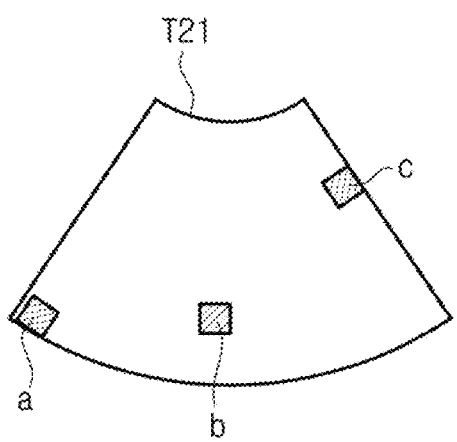

FIGS. 8A and 8B are views for describing an example of the region selection of the medical image and the ultrasound image.

Referring to FIGS. 8A and 8B, the learning apparatus 230 selects a first region from a medical image T11 and a second region from an ultrasound image T21. Here, the first and second regions correspond to each other. The neural network 320 may be trained through comparison of a virtual ultrasound image generated by inputting the first region into the neural network 320 with the second region.

The first region selected from the medical image T11 and the second region selected from the ultrasound image T21 are correlated with each other. That is, the first region may be selected based on a path of ultrasound transmitted to the second region selected from the ultrasound image T21 or a path of echo ultrasound reflected back from the second region.

Each of the first and second regions may include at least one pixel. Further, the first region may have a larger size than the second region. The first region may have more pixels than the second region.

The first and second regions may be constant in size. In detail, the first region may have a length determined based on the maximum range of ultrasound. The ultrasound transmitted from the ultrasound probe to the object ob is gradually attenuated while progressing inside the object ob, and no ultrasound image T21 is obtained from tissue that is out of the maximum range of the ultrasound.

Therefore, information about a region that is not obtained from the ultrasound image T21 is not needed for the training of the neural network 320, and thus the maximum length of the first region selected from the medical image T11 may be shorter than the maximum range of the ultrasound.

The first region may have a width determined according to a resolution of the ultrasound image T21. For example, the higher the resolution of the ultrasound image T21 is, the narrower the width of the first region is.

For example, when a region a of the ultrasound image T21 is selected as the second region, the medical apparatus 210 may select a region A, which corresponds to a straight path between the second region and the ultrasound probe, from the medical image T11 as the first region.

Further, when a region b of the ultrasound image T21 is selected as the second region, the medical apparatus 210 may select a region B, which corresponds to a straight path between the region b and the ultrasound probe, from the medical image T11 as the first region. Here, image information about an ultrasound region that is not obtained within the region B may be set to a preset reference value (e.g., zero).

In addition, when a region c of the ultrasound image T21 is selected as the second region, the medical apparatus 210 may select a region C, which corresponds to a straight path between the region c and the ultrasound probe, from the medical image T11 as the first region. Here, information about an ultrasound image region that is not obtained within the region C may be set to a preset reference value (e.g., zero).

Figure 9A:
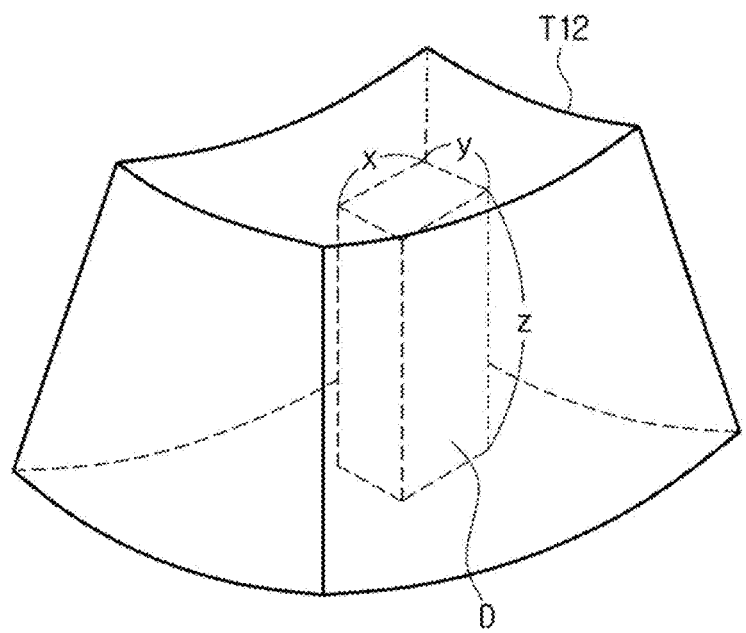
FIGS. 9A and 9B are views for describing an example of region selection of a medical image and an ultrasound image.
Figure 9B:
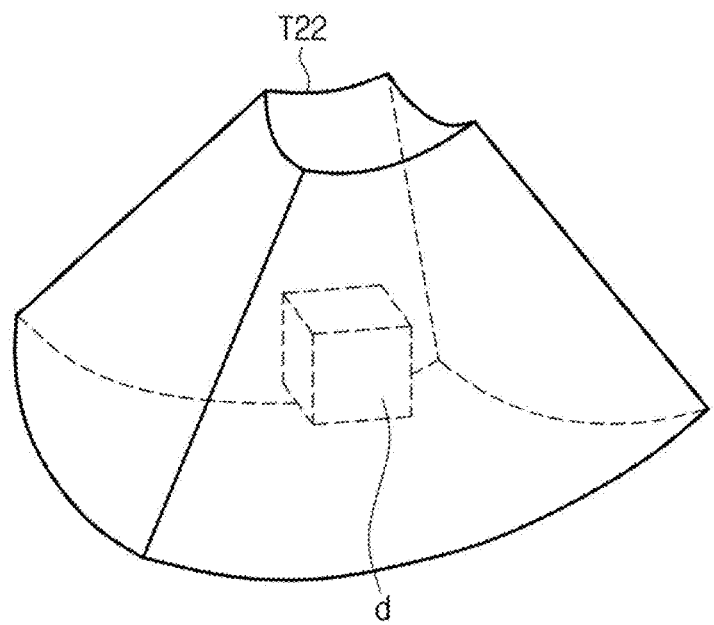

In FIGS. 8A and 8B, each of the first and second regions has been described to be in two dimensions, but may be set to three dimensions. FIGS. 9A and 9B are views for describing another example of the region selection of the medical image and the ultrasound image.

As illustrated in FIGS. 9A and 9B, the learning apparatus 230 selects a first 3D region from a 3D medical image T12 and a second 3D region from a 3D ultrasound image T22, and may train the neural network 320 to recognize the first region as an input of the neural network 320 and the second region as an output of the neural network 320.

The first region selected from the medical image T12 and the second region selected from the ultrasound image T22 are correlated with each other. That is, the first region may be selected based on ultrasound transmitted to the second region selected from the ultrasound image T22 or echo ultrasound reflected back from the second region.

Here, each of the first and second regions may include at least one voxel. Further, the first region may have a larger size than the second region. The first region may have more voxels than the second region.

The first and second regions may be constant in size. In detail, a height z of the first region may be determined based on the maximum range of ultrasound. The ultrasound transmitted from the ultrasound probe to the object ob is gradually attenuated while progressing within the object ob, and no ultrasound image T21 is obtained from tissue that is out of the maximum range of the ultrasound.

Therefore, information about a region that is not obtained from the ultrasound image T22 is not needed for the training of the neural network 320, and thus the maximum height z of the first region selected from the medical image T12 may be shorter than the maximum range of the ultrasound.

A width x and a depth y of the first region may be determined according to a resolution of the ultrasound image T22. For example, the higher the resolution of the ultrasound image T22 is, the narrower the width and/or depth of the first region is.

When a region d of the ultrasound image T22 is selected as the second region, the medical apparatus 210 may select a region D, which corresponds to a straight path between the second region d and the ultrasound probe, from the medical image T12 as the first region.

Figure 10:
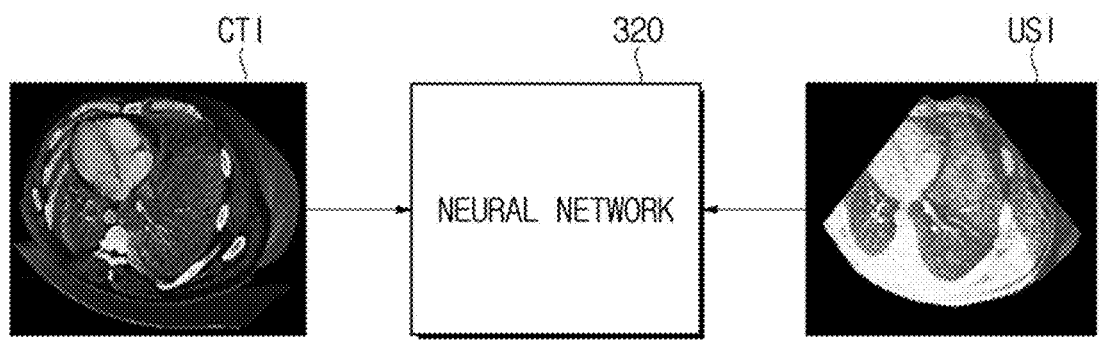
FIG. 10 is a view for describing generation of a virtual ultrasound image by using a neural network according to an exemplary embodiment.
Figure 11:
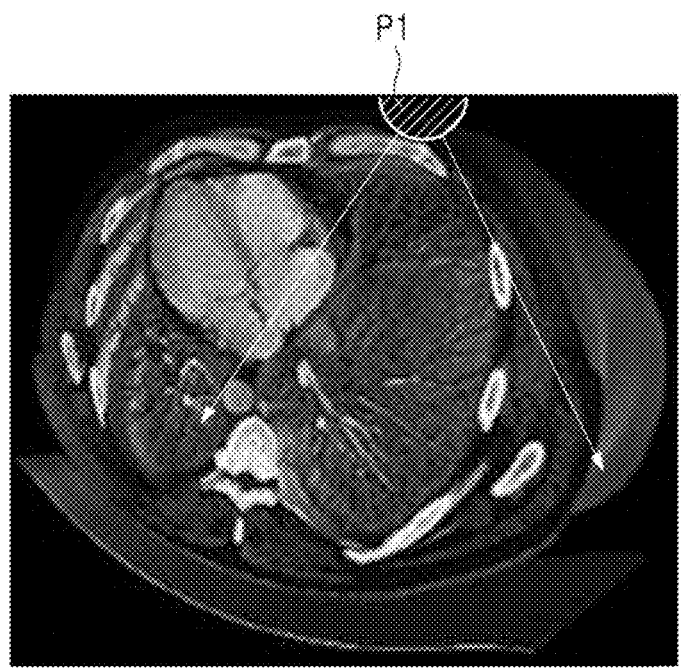
FIG. 11 is a view for describing a virtual probe that is set for a medical image according to an exemplary embodiment.
Figure 12:
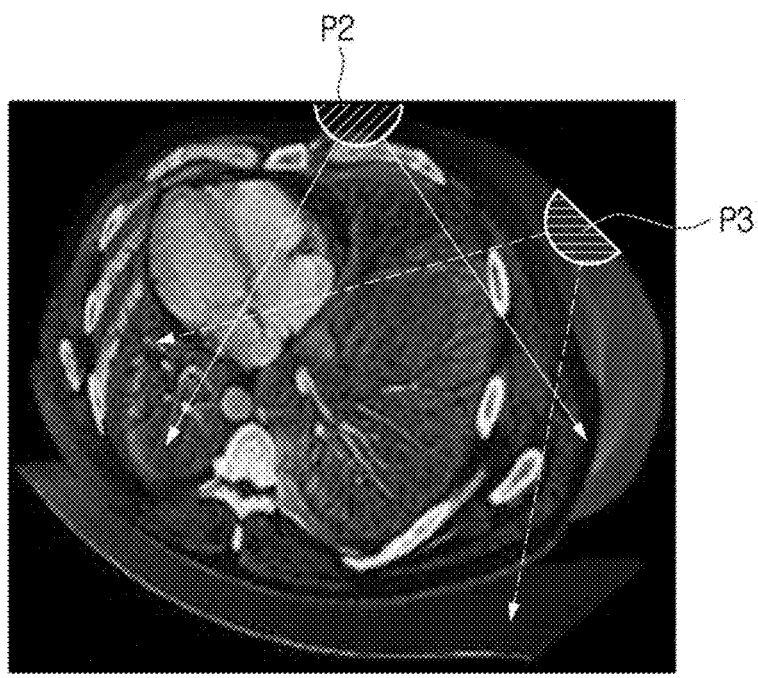
FIG. 12 is a view for describing a virtual probe that is reset for a medical image according to an exemplary embodiment.

FIG. 10 is a view for describing generation of the virtual ultrasound image by using the neural network 320 according to an exemplary embodiment. FIG. 11 is a view for describing a virtual probe that is set for the medical image according to an exemplary embodiment. FIG. 12 is a view for describing the virtual probe that is reset for the medical image according to an exemplary embodiment.

Referring to FIG. 10, the image converting part 310 of the image matcher 300 applies the neural network 320 trained as described above to a medial image CT1, thereby converting the medical image into a virtual ultrasound image corresponding to an ultrasound image US1. The image converting part 310 sets a virtual probe for the medical image and uses the virtual probe as a reference in generating the virtual ultrasound image.

As illustrated in FIGS. 11 and 12, a portion of the medical image used to generate the virtual ultrasound image varies according to a virtual probe position, and thus the virtual probe needs to be set before the virtual ultrasound image is generated. In detail, the virtual ultrasound image generated based on a first virtual probe position P1 and the virtual ultrasound image generated based on a second virtual probe position P2 or a third virtual probe position P3 may be different from each other.

Here, the position of the virtual probe may include coordinates at which the virtual probe is located and/or a direction of the virtual probe.

The position of the virtual probe may be determined by the matching part 330.

The image converting part 310 generates the virtual ultrasound image based on the virtual probe position that is set for the medical image by the matching part 330. The first virtual probe position P1 set by the matching part 330 may be designated by a user, or may be preset according to a predetermined protocol. Further, the first virtual probe position P1 may be determined based on a position of the virtual probe used for previous image matching. Further, the first virtual probe position P1 may be determined based on a position of the actual ultrasound probe 110.

The image converting part 310 may generate the virtual ultrasound image by repeating a process of selecting a first region from the medical image based on the virtual probe set for the medial image, a process of inputting the selected first region into the previously trained neural network 320, and a process of obtaining an image of a second region of the virtual ultrasound image.

Here, a position of the second region of the virtual ultrasound image is determined according to a position of the selected first region. That is, the position of the first region and the position of the second region may have the same correspondence relation as the first region and the second region in the training of the neural network 320.

For example, as illustrated in FIGS. 8A and 8B, when the position of the selected first region is the region A, the position of the second region is the region a. When the position of the selected first region is the region B, the position of the second region is the region b. When the position of the selected first region is the region C, the position of the second region is the region c. Further, as illustrated in FIGS. 9A and 9B, when the position of the selected first region is the region D, the position of the second region is the region d. In this way, the selected first region is input to the trained neural network 320, and the virtual ultrasound image of the second region is obtained.

Further, the first and second regions selected when the virtual ultrasound image is generated may respectively have the same sizes as the first and second regions selected when the neural network 320 is trained.

The matching part 330 matches the medial image and the ultrasound image based on the virtual probe set for the medical image. The ultrasound image varies according to the position of the ultrasound probe 110. For the matching, a virtual probe corresponding to the actual ultrasound probe 110 may be set for a previously obtained medical image, and the medial image and the ultrasound image may be matched with each other based on the position of the virtual probe.

The matching part 330 may determine the position of the virtual probe based on the virtual ultrasound image generated by the image converting part 310 and the ultrasound image obtained by scanning the object ob. That is, the matching part 330 may reset the position of the virtual probe for the medial image based on an error between the ultrasound image obtained by scanning the object ob and the virtual ultrasound image generated by the image converting part 310 such that the ultrasound image obtained by scanning the object ob and the virtual ultrasound image are matched with each other.

To be specific, the matching part 330 sets the virtual probe for the medical image. The matching part 330 calculates an error between the ultrasound image obtained by scanning the object ob and the virtual ultrasound image generated by the image converting part 310 based on the position of the virtual probe set by the matching part 330.

If the calculated error is not greater than a preset reference, it may be determined that the position of the virtual probe corresponds to the position of the actual ultrasound probe 110. Thus, the ultrasound image obtained by scanning the object ob and the medical image obtained from another medical apparatus 210 may be matched with each other based on the position of the virtual probe set for the medical image.

If the ultrasound image and the medical image obtained from the other medical apparatus 210 are matched with each other, the matching part 330 may reset the position of the virtual probe according to movement the ultrasound probe, update the medical image obtained from the other medical apparatus 210, and continuously provide a matched image.

As illustrated in FIG. 12, when the position of the ultrasound probe 110 moves from P2 to P3, the matching part 330 may change the position of the virtual probe from P2 to P3 in response to the movement of the ultrasound probe 110, and continuously provide the matched image corresponding to the changed position of the virtual probe. If the calculated error is greater than the preset reference, the matching part 330 resets the position of the virtual probe set for the medial image. Here, the reset position of the virtual probe may be determined according to the calculated error. For example, movement offset of the reset position may be set according to a degree of the error. Alternatively, the reset position of the virtual probe may be selected by a user.

Figure 13:
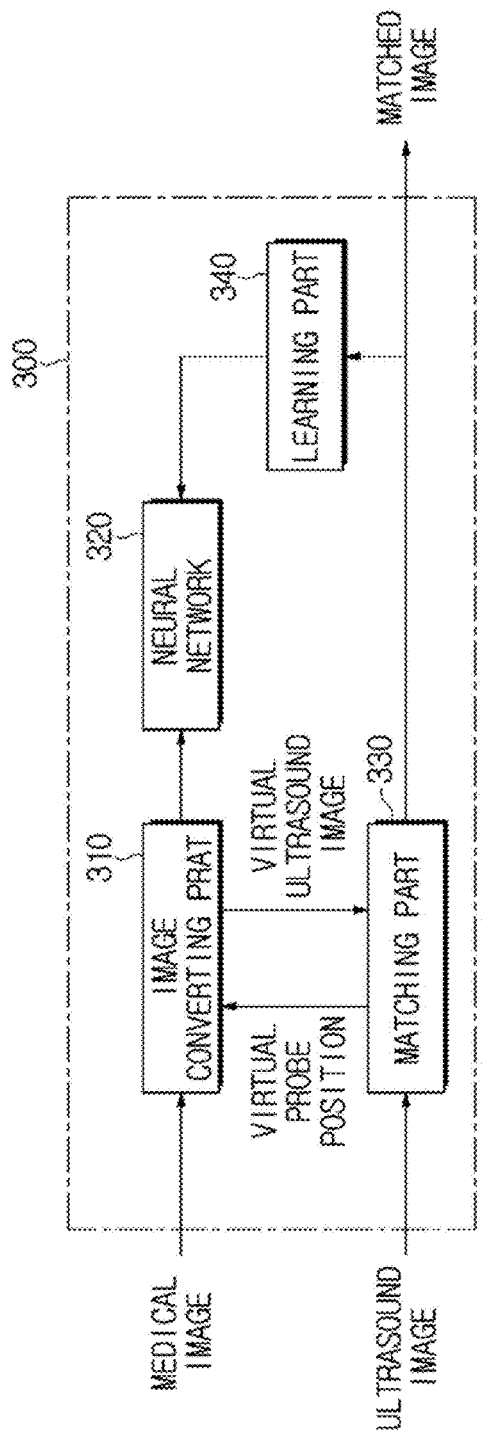
FIG. 13 is a control block diagram for describing an example of an image matcher of an ultrasound imaging apparatus.

FIG. 13 is a control block diagram for describing another example of the image matcher 300 of the ultrasound imaging apparatus 1.

An image matcher 300 according to another exemplary embodiment may further include a learning part 340. As described above, the neural network 320 is trained using the medical image and the ultrasound image that are matched with each other. The learning part 340 may train the neural network 320 again using the medical image and the ultrasound image that are matched by the matching part 330.

Since the neural network 320 is trained again using the medical image and the ultrasound image that are matched by the matching part 330, the neural network 320 can be trained in a more delicate way.

Figure 14:
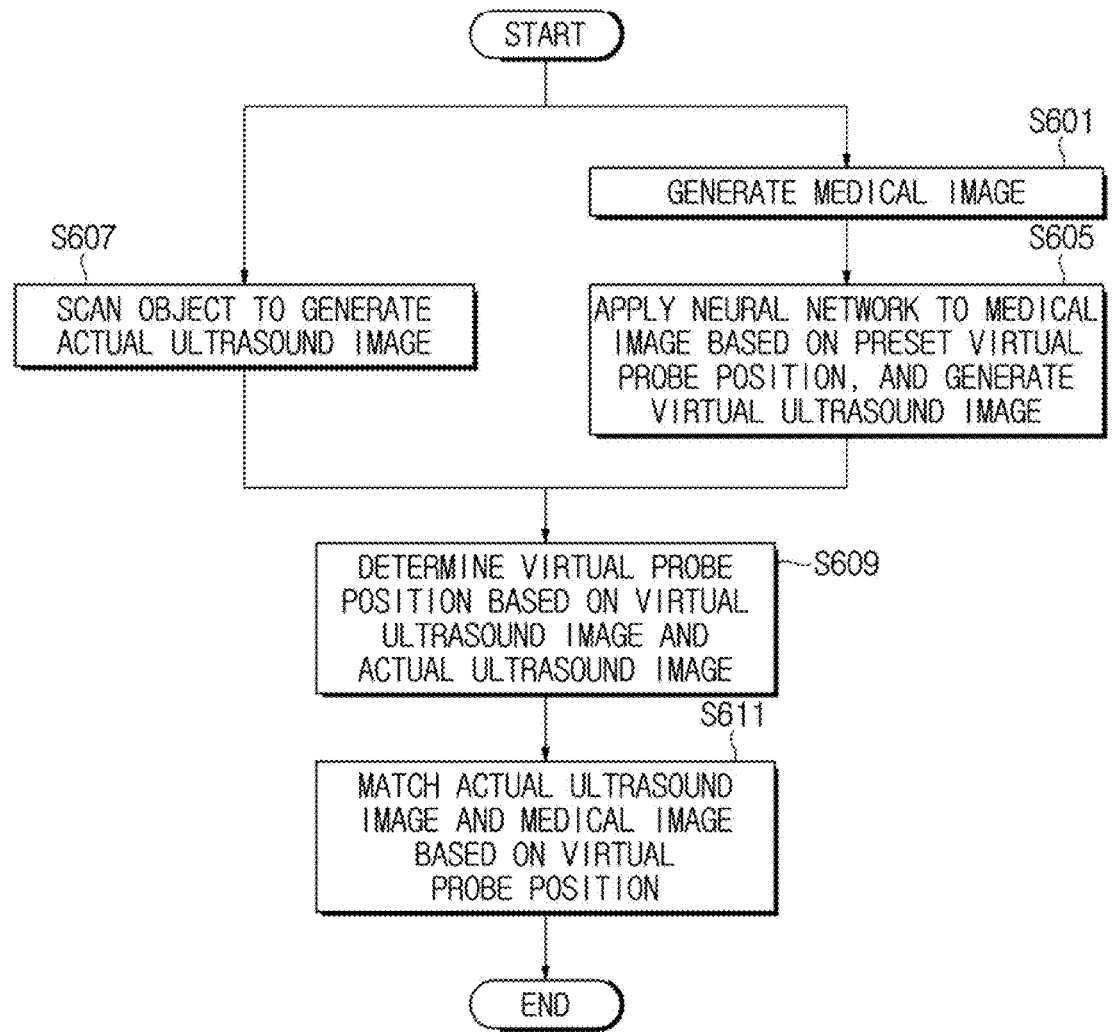
FIG. 14 is a flow chart for describing a method of controlling an ultrasound imaging apparatus according to an exemplary embodiment.

FIG. 14 is a flow chart for describing a method of controlling the ultrasound imaging apparatus 1 according to an exemplary embodiment. Referring to FIG. 14, the ultrasound imaging apparatus 1 obtains a medical image (S601). Here, the medical image is obtained from the other medical apparatus 210 before an ultrasound image of an object ob is obtained. For example, the medial image may be a CT image or an MR image obtained by scanning the object.

The ultrasound imaging apparatus 1 applies the neural network 320 to the medical image based on a preset position of a virtual probe and generates a virtual ultrasound image (S605). Here, the preset position of a virtual probe may be determined according to a certain ultrasound scanning protocol or set by a user. Further, the preset position of the virtual probe may be determined based on a position of the ultrasound probe corresponding to previous image matching. Further, the preset position of the virtual probe may be determined based on a position of the actual ultrasound probe 110.

Here, the medical image is converted into the virtual ultrasound image based on the position of the virtual probe. In detail, the ultrasound imaging apparatus 1 may convert the medical image into the virtual ultrasound image by repeating a process of selecting a first region from the medical image based on the position of the virtual probe, a process of inputting the selected first region into the neural network 320, and a process of converting the selected first region into a second region of the virtual ultrasound image.

The ultrasound imaging apparatus 1 scans the object ob to obtain an actual ultrasound image (S607). The actual ultrasound image may be generated based on echo ultrasound reflected back from the object ob.

The ultrasound imaging apparatus 1 determines the position of the virtual probe based on the virtual ultrasound image and the actual ultrasound image (S609). As described above, the actual ultrasound image is changed according to the position (e.g., coordinates and/or direction) of the ultrasound probe 110. To match the medical image and the ultrasound image, the virtual probe corresponding to the ultrasound probe 110 needs to be set for the medial image.

In this way, the ultrasound imaging apparatus 1 may determine the position of the virtual probe based on the virtual ultrasound image and the actual ultrasound image (S609). The determination of the position of the virtual probe will be described in detail with reference to FIG. 15.

The ultrasound imaging apparatus 1 matches the actual ultrasound image and the medical image based on the determined position of the virtual probe (S611). For example, a transform function determined based on the position of the virtual probe may be applied to the medical image, and a coordinate system of the medical image may be substantially identical to that of the ultrasound image.

As described above, the actual ultrasound image is changed according to movement of the position of the ultrasound probe 110. The ultrasound imaging apparatus 1 may update the position of the virtual probe applied to the medical image according to movement of the position of the ultrasound probe 110 and continuously provide the medical image matched with the actual ultrasound image.

Figure 15:
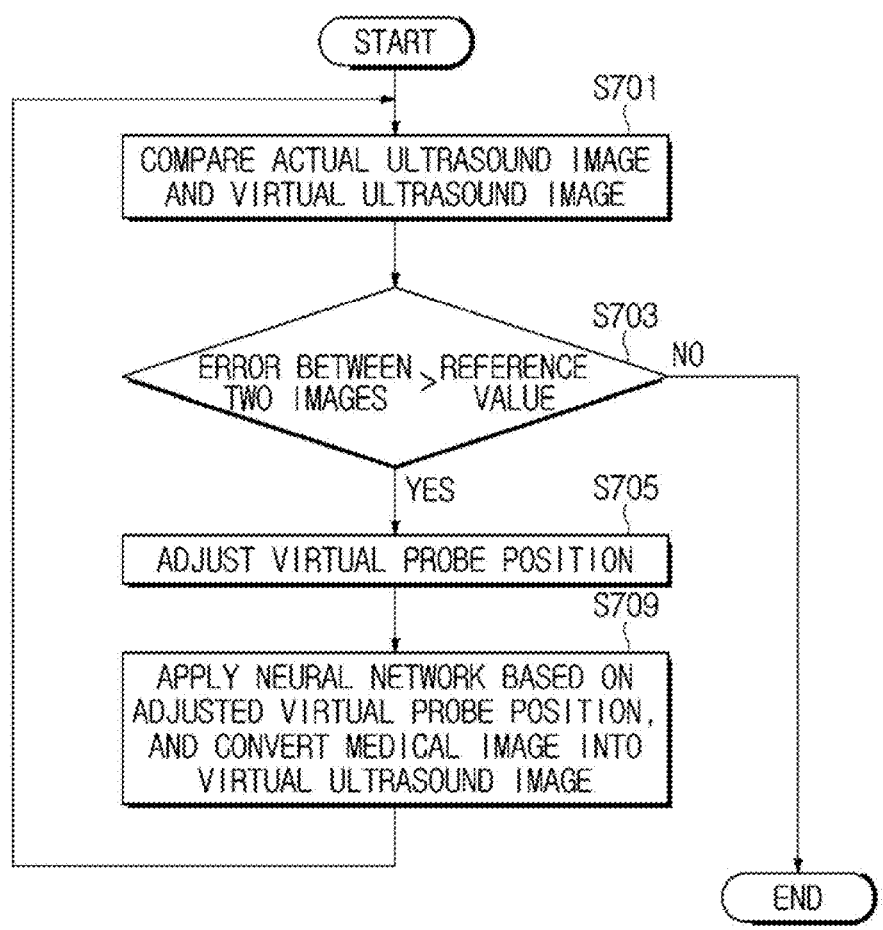
FIG. 15 is a flow chart for describing determination of a position of a virtual probe according to an exemplary embodiment.

FIG. 15 is a flow chart for describing operation S609 of FIG. 14.

Referring to FIG. 15, the ultrasound imaging apparatus 1 compares the actual ultrasound image with the virtual ultrasound image generated by applying the neural network to the medial image based on the position of the virtual probe of operation S605 (S701). Here, there is no limitation to a method of comparing the actual ultrasound image with the virtual ultrasound image. Further, a region of interest within the actual ultrasound image may be compared with the virtual ultrasound image. The ultrasound imaging apparatus 1 determines whether an error between the two images is greater than a reference value (S703). Here, the reference value may be preset or selected by a user.

If it is determined that the error between the two images is greater than the reference value ('Yes' of S703), the ultrasound imaging apparatus 1 adjusts the position of the virtual probe (S705). Here, the adjustment of the position of the virtual probe may be determined according to the calculated error. For example, movement offset of the position of the virtual probe may be determined according to a degree of the error. Further, the position of the reset virtual probe may be determined by a user. When the position of the virtual probe is reset by the user, the ultrasound imaging apparatus 1 may simultaneously display the actual ultrasound image and the virtual ultrasound image to allow the user to easily adjust the position of the virtual probe.

The ultrasound imaging apparatus 1 applies the neural network to the medical image based on the adjusted position of the virtual probe to convert the medical image into the virtual ultrasound image (S709). Here, the virtual ultrasound image may be generated by the same or similar method as in operation S605 of FIG. 14.

The ultrasound imaging apparatus 1 compares the actual ultrasound image with the virtual ultrasound image generated by applying the neural network to the medical image based on the adjusted position of the virtual probe (S701). That is, the ultrasound imaging apparatus 1 determines the position of the virtual probe by repeating operations S701 to S709 until the error between the two images is equal to or less than the reference value.

Figure 16:
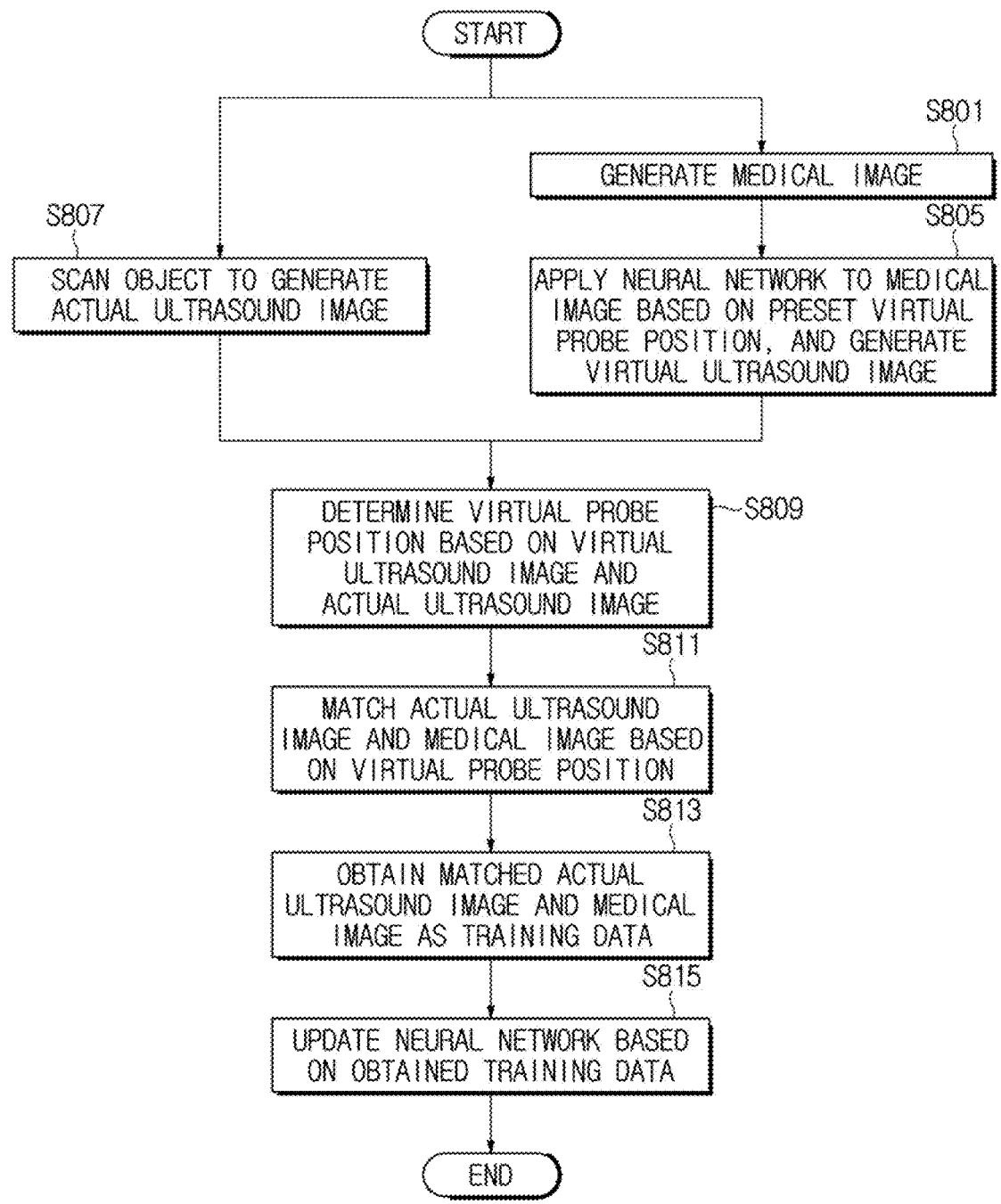
FIG. 16 is a flow chart for describing a method of controlling an ultrasound imaging apparatus according to an exemplary embodiment.

FIG. 16 is a flow chart for describing a method of controlling the ultrasound imaging apparatus according to another exemplary embodiment.

Referring to FIG. 16, the ultrasound imaging apparatus 1 obtains a medical image (S801). The ultrasound imaging apparatus 1 applies the neural network 320 to the medical image based on a preset position of a virtual probe and generates a virtual ultrasound image (S805).

The ultrasound imaging apparatus 1 scans an object ob to obtain an actual ultrasound image (S807). The actual ultrasound image may be generated based on echo ultrasound reflected back from the object ob.

The ultrasound imaging apparatus 1 determines a position of a virtual probe based on the virtual ultrasound image and the actual ultrasound image (S809).

In this way, the ultrasound imaging apparatus 1 may determine the position of the virtual probe based on the virtual ultrasound image and the actual ultrasound image (S809).

The ultrasound imaging apparatus 1 matches the actual ultrasound image and the medical image based on the determined position of the virtual probe (S811).

The ultrasound imaging apparatus 1 obtains training data from the actual ultrasound image and the medical image that are matched with each other (S813) and update the neural network 320 based on the obtained training data (S815). As described above, the training data of the neural network 320 are the medical image and the ultrasound image that are matched with each other. Therefore, in the ultrasound imaging apparatus 1, the medical image and the ultrasound image that are matched with each other can be obtained as the training data.

The ultrasound imaging apparatus 1 updates the neural network 320 based on the obtained training data. For example, the ultrasound imaging apparatus 1 may update the neural network 320 based on the training data at a preset period, or the ultrasound imaging apparatus 1 may update the neural network 320 when the training data of a preset volume are obtained. Due to the update, the neural network 320 may be additionally trained to provide a more precise virtual ultrasound image. Further, the neural network 320 may be customized to the user by the update.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. An ultrasound imaging apparatus comprising:
    an image generator, implemented by at least one processor, configured to scan an object to obtain an ultrasound image;
    a matching part, implemented by the at least one processor, configured to set a position of a virtual probe for a medical image, wherein the medical image is obtained from a medical apparatus having a modality different from that of the ultrasound imaging apparatus; and
    an image converting part, implemented by the at least one processor, configured to convert the medical image into a virtual ultrasound image, based on the position of the virtual probe that is set for the medical image, using a neural network that is previously trained, wherein the neural network uses a plurality of ultrasound images and a plurality of medical images which are matched to each other to learn a correlation between the plurality of ultrasound images and the plurality of medical images, and is trained to output a correlated ultrasound image when the medical image is input as an input data,
    wherein the matching part is configured to match the ultrasound image with the medical image that corresponds to the position of the virtual probe and to reset the position of the virtual probe based on an error between the ultrasound image and the virtual ultrasound image.

2. The ultrasound imaging apparatus according to claim 1, wherein the image converting part is configured to generate the virtual ultrasound image based on the position of the virtual probe.

3. The ultrasound imaging apparatus according to claim 2, wherein the image converting part is configured to select a first region from the medical image based on the position of the virtual probe, to input the selected first region into the neural network, and to obtain an image of a second region of the virtual ultrasound image.

4. The ultrasound imaging apparatus according to claim 3, wherein the first region has a length determined based on a range of ultrasound transmission in the object.

5. The ultrasound imaging apparatus according to claim 3, wherein the first region has a width determined based on a resolution of the ultrasound image.

6. The ultrasound imaging apparatus according to claim 1, further comprising:
    a learning part, implemented by the at least one processor, configured to train the neural network using the ultrasound image and the medical image that are matched with each other by the matching part.

7. The ultrasound imaging apparatus according to claim 6, wherein the learning part is configured to train the neural network such that the ultrasound image matched with the medical image is output as the virtual ultrasound image in response to an input of the medical image.

8. The ultrasound imaging apparatus according to claim 1, wherein the medical image includes at least one of a magnetic resonance (MR) image, a computed tomography (CT) image, a positron emission tomography (PET) image, and a single photon emission computed tomography (SPECT) image.

9. The ultrasound imaging apparatus according to claim 1, wherein the neural network has a multilayer perceptron structure.

10. The ultrasound imaging apparatus according to claim 1, further comprising:
    a display configured to display the medical image that is matched with the ultrasound image together with the ultrasound image.

11. A method of controlling an ultrasound imaging apparatus, the method comprising:
    scanning an object to obtain an ultrasound image;
    setting a position of a virtual probe for a medical image, wherein the medical image is obtained from a medical apparatus having a modality different from that of the ultrasound imaging apparatus;
    generating a virtual ultrasound image by converting the medical image into the virtual ultrasound image, based on the position of the virtual probe that is set for the medical image, using a neural network that is previously trained, wherein the neural network uses a plurality of ultrasound images and a plurality of medical images which are matched to each other to learn a correlation between the plurality of ultrasound images and the plurality of medical images, and is trained to output a correlated ultrasound image when the medical image is input as an input data;
    matching the ultrasound image with the medical image that corresponds to the position of the virtual probe; and
    resetting the position of the virtual probe based on an error between the ultrasound image and the virtual ultrasound image.

12. The method according to claim 11, wherein the converting comprises converting the medical image into the virtual ultrasound image based on the position of the virtual probe.

13. The method according to claim 11, wherein the generating comprises generating a second virtual ultrasound image by applying the neural network to the medical image based on the reset position of the virtual probe.

14. The method according to claim 13, wherein the matching comprises matching the medical image and the ultrasound image based on the reset position of the virtual probe in response to the error between the ultrasound image and the second virtual ultrasound image being equal to or less than a reference value.

15. The method according to claim 13, wherein the converting comprises:
    selecting a first region from the medical image based on the position of the virtual probe; and
    inputting the selected first region into the neural network to obtain an image of a second region of the virtual ultrasound image.

16. The method according to claim 15, wherein the first region has a length determined based on a range of ultrasound transmission in the object, and a width determined based on a resolution of the ultrasound image.

17. The method according to claim 11, further comprising:
    training the neural network using the medical image and the ultrasound image that are matched with each other.

18. The method according to claim 11, wherein the medical image comprises at least one of a magnetic resonance (MR) image, a computed tomography (CT) image, a positron emission tomography (PET) image, and a single photon emission computed tomography (SPECT) image.

* * * * *